(12) United States Patent
Kelly

(10) Patent No.: US 11,766,541 B2
(45) Date of Patent: Sep. 26, 2023

(54) PULMONARY EMBOLISM APPARATUS

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 223 days.

(21) Appl. No.: 16/953,789

(22) Filed: Nov. 20, 2020

(65) Prior Publication Data

US 2021/0069461 A1 Mar. 11, 2021

Related U.S. Application Data

(60) Continuation of application No. 15/876,865, filed on Jan. 22, 2018, now Pat. No. 10,857,326, which is a
(Continued)

(51) Int. Cl.
*A61M 25/00* (2006.01)
*A61B 5/0215* (2006.01)
(Continued)

(52) U.S. Cl.
CPC ......... *A61M 25/003* (2013.01); *A61B 5/0215* (2013.01); *A61B 5/02158* (2013.01);
(Continued)

(58) Field of Classification Search
CPC .. A61M 25/003; A61M 5/142; A61M 5/1723; A61M 25/0068; A61M 25/0075;
(Continued)

(56) References Cited

U.S. PATENT DOCUMENTS 5,916,193 A * 6/1999 Stevens ............... A61M 25/007
604/509
8,298,156 B2 10/2012 Manstrom
(Continued)

FOREIGN PATENT DOCUMENTS

JP H07-255853 A 10/1995
JP 2011-083596 A 4/2011
(Continued)

OTHER PUBLICATIONS

International Search Report and Written Opinion for corresponding PCT application No. PCT/US2016/027439, dated Jul. 20, 2016*.
(Continued)

*Primary Examiner* — James D Ponton
(74) *Attorney, Agent, or Firm* — McDonnell Boehnen Hulbert & Berghoff LLP

(57) ABSTRACT

An apparatus and methods for use are provided, where the apparatus includes: (a) a first catheter having a proximal end and a distal end, and wherein a distal portion of the first catheter includes a first one or more outlets, (b) a first tubular housing having a proximal end and a distal end, wherein the first tubular housing is coupled to the first catheter proximal to the at least one first outlet, (c) one or more pressure sensors coupled to the distal end of the first tubular housing, and (d) a second catheter having a proximal end and a distal end, wherein a distal portion of the second catheter includes a second one or more outlets, and wherein the distal end of the second catheter is configured to be positioned substantially within one of (i) the first catheter or (ii) a second tubular housing coupled to one or more of the first catheter and the first tubular housing, when the second catheter is in a first position.

28 Claims, 8 Drawing Sheets

Related U.S. Application Data division of application No. 15/098,908, filed on Apr. 14, 2016, now Pat. No. 10,166,362.

(60) Provisional application No. 62/270,943, filed on Dec. 22, 2015, provisional application No. 62/147,892, filed on Apr. 15, 2015.

(51) Int. Cl.

| | | |
|---|---|---|
| *A61M 25/04* | (2006.01) | |
| *A61B 5/00* | (2006.01) | |
| *A61M 5/142* | (2006.01) | |
| *A61M 5/172* | (2006.01) | |
| *A61M 25/10* | (2013.01) | |
| *A61M 25/01* | (2006.01) | |

(52) U.S. Cl.
CPC ........... *A61B 5/6852* (2013.01); *A61M 5/142* (2013.01); *A61M 5/1723* (2013.01); *A61M 25/0068* (2013.01); *A61M 25/0075* (2013.01); *A61M 25/04* (2013.01); *A61M 25/10* (2013.01); *A61M 25/007* (2013.01); *A61M 2005/1726* (2013.01); *A61M 2025/0002* (2013.01); *A61M 2025/004* (2013.01); *A61M 2025/0004* (2013.01); *A61M 2025/0037* (2013.01); *A61M 2025/0039* (2013.01); *A61M 2025/0175* (2013.01); *A61M 2025/1045* (2013.01); *A61M 2205/3379* (2013.01); *A61M 2230/30* (2013.01)

(58) Field of Classification Search
CPC .... A61M 25/04; A61M 25/10; A61M 25/007; A61M 2005/1726; A61M 2025/0002; A61M 2025/0004; A61M 2025/0037; A61M 2025/0039; A61M 2025/004; A61M 2025/0175; A61M 2025/1045; A61M 2205/3379; A61M 2230/30; A61B 5/0215; A61B 5/02158; A61B 5/6852

See application file for complete search history.

(56) References Cited

U.S. PATENT DOCUMENTS

| | | | |
|---|---|---|---|
| 2003/0032936 A1 | 2/2003 | Lederman | |
| 2003/0104073 A1* | 6/2003 | Johansson | A61K 33/00 604/509 |
| 2003/0149395 A1 | 8/2003 | Zawacki | |
| 2004/0030281 A1* | 2/2004 | Goble | A61M 27/00 604/40 |
| 2004/0127855 A1* | 7/2004 | Core | A61M 39/0606 604/167.04 |
| 2005/0043669 A1* | 2/2005 | Rosenberg | A61B 5/032 604/9 |
| 2005/0245882 A1 | 11/2005 | Elkins | |
| 2006/0030814 A1 | 2/2006 | Valencia | |
| 2006/0047266 A1 | 3/2006 | Elkins | |
| 2006/0079859 A1 | 4/2006 | Elkins | |
| 2006/0149350 A1 | 7/2006 | Patel | |
| 2007/0005018 A1 | 1/2007 | Tekbuchava | |
| 2007/0088286 A1* | 4/2007 | Brier | A61M 5/1408 604/189 |
| 2007/0287967 A1 | 12/2007 | Hekmat | |
| 2008/0051714 A1* | 2/2008 | Moberg | A61M 5/1413 604/135 |
| 2008/0221551 A1 | 9/2008 | Goodson | |
| 2009/0205189 A1 | 8/2009 | Nimkar | |
| 2009/0305990 A1 | 12/2009 | Goodson | |
| 2009/0306625 A1 | 12/2009 | Pereira-Kamath | |
| 2009/0318857 A1 | 12/2009 | Goodson, IV | |
| 2010/0217304 A1* | 8/2010 | Angel | A61M 25/0029 600/301 |
| 2011/0092955 A1* | 4/2011 | Purdy | A61B 5/026 604/523 |
| 2013/0281761 A1 | 10/2013 | Kapur | |
| 2014/0025037 A1* | 1/2014 | Elkins | A61M 25/0071 604/508 |

FOREIGN PATENT DOCUMENTS

| | | |
|---|---|---|
| JP | 2014-064765 A | 4/2014 |
| WO | 2004034767 A2 | 4/2004 |
| WO | 2004107965 A2 | 12/2004 |
| WO | 2006036944 A2 | 4/2006 |
| WO | 2007044907 A2 | 4/2007 |
| WO | 2007146825 A2 | 12/2007 |
| WO | 2011119879 A1 | 9/2011 |
| WO | 2014-025825 A1 | 2/2014 |

OTHER PUBLICATIONS

St. Jude Medical, CardioMEMS™ HF System Brochure, available at www.sjm.com/cardiomems as of Dec. 18, 2015*.

* cited by examiner

PULMONARY EMBOLISM APPARATUS

RELATED APPLICATIONS

This application is a continuation of U.S. Ser. No. 15/876,865, filed Jan. 18, 2018, which is a divisional application of U.S. Ser. No. 15/098,908, filed Apr. 14, 2016, which claims priority to (i) U.S. Provisional Application No. 62/147,892, filed on Apr. 15, 2015, and (ii) U.S. Provisional Application No. 62/270,943, filed on Dec. 22, 2015, the contents of each of which are hereby incorporated by reference in their entirety.

BACKGROUND OF THE INVENTION

Pulmonary embolism is a blockage of the main artery (saddle emboli) of the lung or multiple bilateral branches by a substance that has travelled from elsewhere in the body through the bloodstream. The resulting obstruction of the blood flow through the lungs may cause increased pressure on the right ventricle of the heart that may lead to one or more of the following: dyspnea (shortness of breath), tachypnea (rapid breathing), chest pain of a "pleuritic" nature (worsened by breathing), and/or cough and hemoptysis (i.e., coughing up blood). The occurrence of this condition is about 1-2 per 1000 people per capita in the United States, and the likelihood of having a pulmonary embolism increases with age. After 80 years of age, a pulmonary embolism carries a 30% thirty day mortality using current standard of care of anticoagulation. Anticoagulant therapy is a common treatment for pulmonary embolisms. However, delivery of the treatment solution to the location in the pulmonary artery where the embolism is located may be clumsy and less than ideal. For example, current treatment methods include creating multiple holes in a unilateral femoral vein or multiple holes in bilateral femoral veins in order to obtain access in order to place multiple catheters in the right and left pulmonary arteries. Such methods may increase the risk of bleeding during and after treatment. Multiple access sites in a single femoral vein can increase the risk of hematoma. Further, when the systemic or catheter-directed anticoagulant is being actively administered in vivo, there is no way to know when the blockage has been completely removed thereby needlessly prolonging treatment in some cases. This extended treatment may further result in exposure of a patient to the lytic thereby increasing their risk of a devastating bleeding complication, such as cerebral hemorrhage.

Pulmonary hypertension is a type of high blood pressure that affects the arteries in the lungs and the right side of the heart. Pulmonary hypertension begins when pulmonary arteries and capillaries become narrowed, blocked, or destroyed. This makes it harder for blood to flow through the lungs, and raises pressure within the lungs' arteries. As the pressure builds, the right ventricle of the heart must work harder to pump blood through the lungs, eventually leading to right-side heart failure and hypoxia. Pulmonary hypertension is a serious illness that becomes progressively worse and is sometimes fatal. Signs and symptoms include shortness of breath, fatigue, dizziness or fainting, chest pressure or pain, swelling in the ankles, bluish color in the lips, and racing pulse or heart palpitations.

Right heart catheterization may be helpful for diagnosing pulmonary hypertension. During such a procedure, a catheter is placed into a vein in the patient's neck or groin. The catheter is then threaded into the patient's right ventricle and pulmonary artery. Right heart catheterization allows a medical professional to directly measure the pressure in the main pulmonary arteries and right ventricle. Such a procedure may also be used to monitor the effect medication may have on pulmonary hypertension of the patient. With a pressure sensing line in the pulmonary arteries, if the operator injects a drug and notes a decrease in pulmonary artery pressures, the medical professional may determine that that drug may be a good option for the particular patient.

There are a few medications that can be used to treat pulmonary hypertension with varying degrees of efficacy. Blood vessel dilators (vasodilators) open narrowed blood vessels. One of the most commonly prescribed vasodilators for pulmonary hypertension is epoprostenol (Flolan). A drawback is that the effect may only last a few minutes. This drug is continuously injected through an intravenous catheter via a small pump worn on the belt or shoulder. The patient may have to mix their own medications and may require frequent follow-up from a medical professional. A related drug, iloprost (Ventavis) can be inhaled every three hours through a nebulizer, a machine that vaporizes the medication. Inhalation of the drug may permit the drug to be delivered directly to the lungs. An alternative drug may include, endothelin receptor antagonists that may reverse the effects of endothelin, a substance in the walls of blood vessels that causes them to narrow. Another medication that may stop the narrowing of blood vessels is Ambrisentan (Letairis). Sildenafil (Viagra) and tadalafil (Cialis) may be used and work to open the blood vessels in the lungs. In addition, high-dose calcium channel blockers are drugs that may help relax the muscles in the walls of blood vessels. They include medications such as amlodipine (Norvasc), diltiazem (Cardizem, Tiazac), and nifedipine (Adalat, Procardia). Only a small number of patients suffering from pulmonary hypertension respond to calcium channel blockers. Diuretics can also be used. They are commonly known as water pills, and help eliminate excess fluid from the body. This may reduce the amount of work your heart has to do and may also help limit fluid buildup in the lungs.

Surgical options are limited for patients suffering from pulmonary hypertension. Atrial septostomy is an open-heart surgery that may be an option, but only for patients who do not respond to medication. In an atrial septostomy, a surgeon may create an opening between the left and right chambers of the heart to relieve pressure on the right side of the heart. Atrial septostomy may have serious complications including heart rhythm abnormalities (arrhythmias). Transplantation is another option in some cases for younger patients with idiopathic pulmonary hypertension. However, transplantation carries significant risks including rejection of the transplanted organ and serious infection, and the patient must take immunosuppressant drugs for the rest of their life to help reduce the chance of rejection.

Heart failure may occur when abnormal cardiac function causes failure of the heart to pump blood at a rate sufficient for metabolic requirements under normal filling pressure. Heart failure may be characterized clinically by breathlessness, effort intolerance, fluid retention, and poor survival. Heart failure may be caused by systolic or diastolic dysfunction. For example, left ventricular systolic dysfunction may be defined as left ventricular ejection fraction <0.40. Diastolic heart failure may be defined as a condition in which the heart does not fill with blood properly, and it may be difficult to diagnose. Directly monitoring pulmonary artery pressure via a procedure called right-heart catheterization is standard-of-care for hospitalized heart failure patients. However, in view of the chronic nature of heart failure, the patient may spend many days outside of the hospital, making at-home monitoring important. Systems have been developed for micro-electromechanical monitoring of pulmonary artery pressure as a means for early at home diagnosis of heart failure events, but they require the patient to visit their physician in the event of an episode in order to receive an injection of heart failure medication in order to prevent hospital admission.

SUMMARY OF THE INVENTION

The present invention is directed to a device that improves the ability to monitor pulmonary artery pressures to aid in clinical decision making. For example, there is currently no convenient way to monitor right-side heart strain and pulmonary artery pressures in real time, and current treatment methods typically require long treatment durations to ensure that an embolism has cleared. The longer patients are exposed to medications or treatment solutions that dissolve clots, the greater the risk of internal bleeding. Internal bleeding can be devastating in situations such as intracranial hemorrhage. Therefore, determining when the embolism has been sufficiently treated would be advantageous to shorten delivery time for the treatment solution. The apparatus described herein may be used for improving the delivery of treatment solutions to the pulmonary arteries for treatment of pulmonary embolisms. Further, in one embodiment, the apparatus may include a mechanism to detect when healthy blood flow through the pulmonary arteries is reestablished, thereby indicating the treatment is completed.

Thus, in a first aspect, the present invention provides an apparatus including (a) a first catheter having a proximal end and a distal end, and wherein a distal portion of the first catheter includes at least one first outlet, (b) a first tubular housing having a proximal end and a distal end, wherein the first tubular housing is coupled to the first catheter proximal to the at least one first outlet, (c) one or more pressure sensors coupled to the distal end of the first tubular housing, and (d) a second catheter having a proximal end and a distal end, wherein a distal portion of the second catheter includes at least one second outlet, and wherein the distal end of the second catheter is configured to be positioned substantially within one of (i) the first catheter or (ii) a second tubular housing coupled to one or more of the first catheter and the first tubular housing, when the second catheter is in a first position.

In a second aspect, the present invention also provides a method comprising: (a) introducing the apparatus of the first aspect within a pulmonary artery, (b) introducing a guide wire into the second catheter of the apparatus, (c) moving the second catheter along the guide wire such that the distal end of the second catheter extends beyond the distal end of the first tubular housing, and (d) advancing a treatment solution out of the at least one first outlet of the first catheter and the at least one second outlet of the second catheter and into the opposite pulmonary artery.

In a third aspect, the present invention can be coupled to a subcutaneously implantable pump. The pump may include a reservoir which can be filled with a therapeutic or drug solution. When a pressure sensor senses an elevated pulmonary artery pressure, the sensor may communicate with a controller which activates the pump to deliver the therapeutic solution to the pulmonary arteries until the pressure sensor senses an acceptable normal pulmonary artery pressure and communicates with the controller which subsequently modulates the flow rate or turns the pump off. Pulmonary hypertension can also be monitored as a means of detecting episodes of heart failure. As such, the present invention could also be used in conjunction with medications appropriate for heart failure patients. In such an example, when the system detects elevated pulmonary artery pressure it will communicate with the pump to infuse heart failure medications.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Figure 1A:
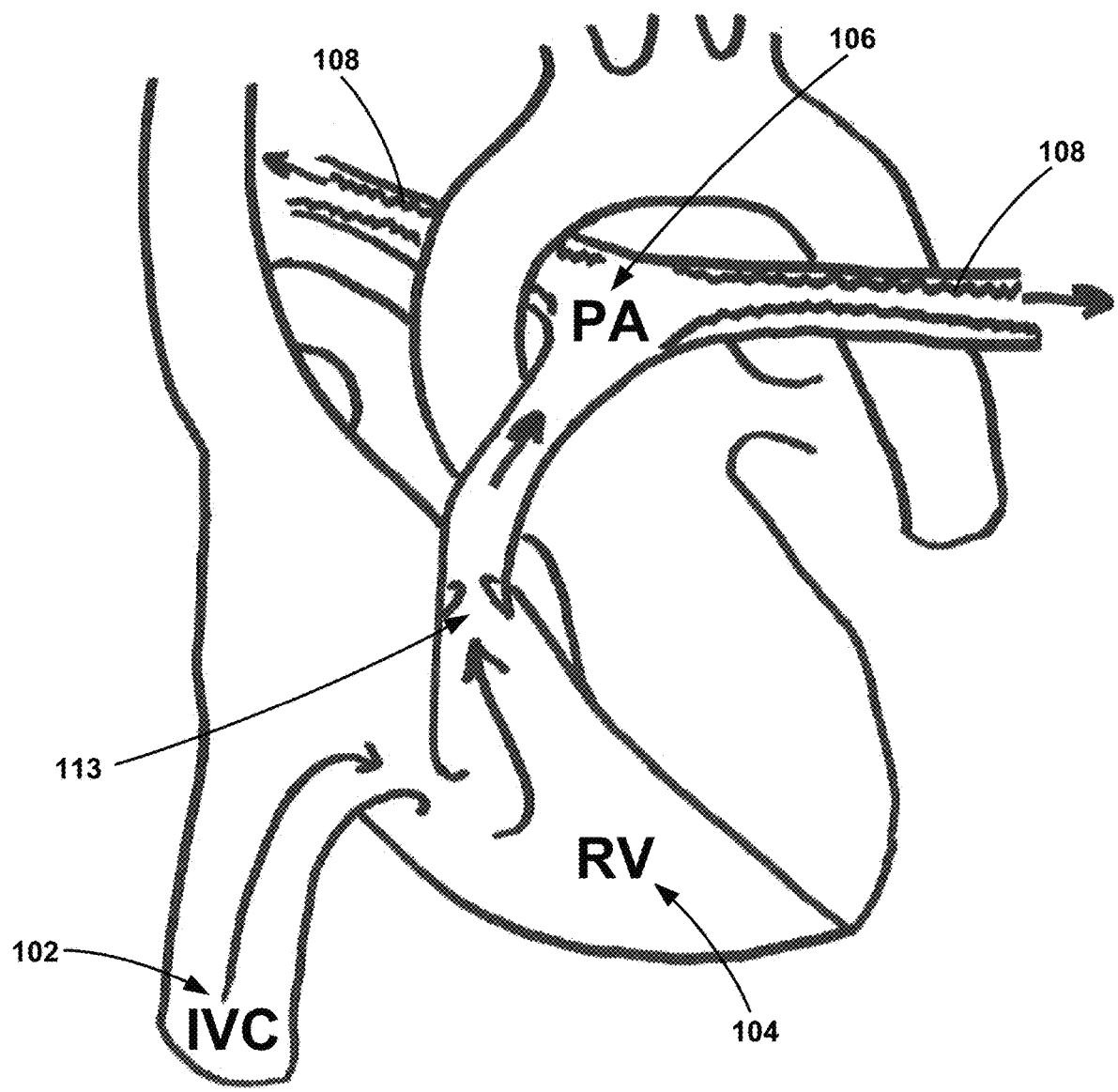
FIG. 1A illustrates a schematic of the cardiopulmonary structure.

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means+/−5%.

As used herein, "distal" with respect to a portion of the apparatus means the end of the device (when in use) nearer the treatment zone (e.g., the pulmonary artery) of the subject and the term "proximal" means the portion of the device (when in use) further away from the targeted lumen of the subject and nearer the access site and the operator.

As used herein, "lumen" refers to a passage within an arterial structure such as the pulmonary arteries or the passage within the tubular housings or drug delivery catheters.

As used herein, "French" refers to a unit of measurement for a catheter. A round catheter of 1 French has an external diameter of ⅓ mm, and therefore the diameter of a round catheter in millimeters can be determined by dividing the French size by 3.

As used herein, "treatment solution" refers to any flowable material that may be administered into the pulmonary artery. When the drug solution comprises a therapeutic to be administered to a patient, any suitable drug that can be administered in solution can be used. As one example, the treatment solution includes lytic agents. In various non-limiting embodiments, the therapeutic may comprise sirolimus, heparin, and cell-based therapies; and antineoplastic, anti-inflammatory, antiplatelet, anticoagulant, antifibrin, antithrombin, antimitotic, antibiotic, vasodisle, antiallergic thrombolytic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), thrombolytic-urokinase, streptokinase, TPA (Tissue Plasminogen Activator) colchicine, proteins, peptides, vasodilators-nitro-based drug, Ca++ channel blocker, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin. Treatment solutions that are of interest for the pulmonary arteries include vasodilators including epoprostenol (Flolan) and iloprost (Ventavis) and endothelin receptor antagonists such as Ambrisentan (Letairis). Additional therapeutic solutions that can be infused into the pulmonary arteries include Sildenafil (Viagra) and Tadalafil (Cialis), high-dose calcium channel blockers including Amlodipine (Norvasc), Diltiazem (Cardizem, Tiazac), and Nifedipine (Adalat, Procardia), and various diuretics. Various nitrates for coronary artery disease can also be beneficial when infused, including isosorbide dinitrate (Dilatrate, Isordil), isosorbide mononitrate (ISMO), and nitroglycerine (Nitro-Dur, Nitrolingual, and Nitrostate). Therapeutics that can be infused with the present invention for treating heart failure include inotropes such as dabutamine, angiotensin-convertine enzyme inhibitors, angiotensin II receptor blockers, beta blockers, diuretics, aldosterone antagonists, and digoxin. In addition, non-therapeutic fluids, such as water, may be used, if the apparatus is being used in a teaching model or training demonstration for example.

Figure 1B:
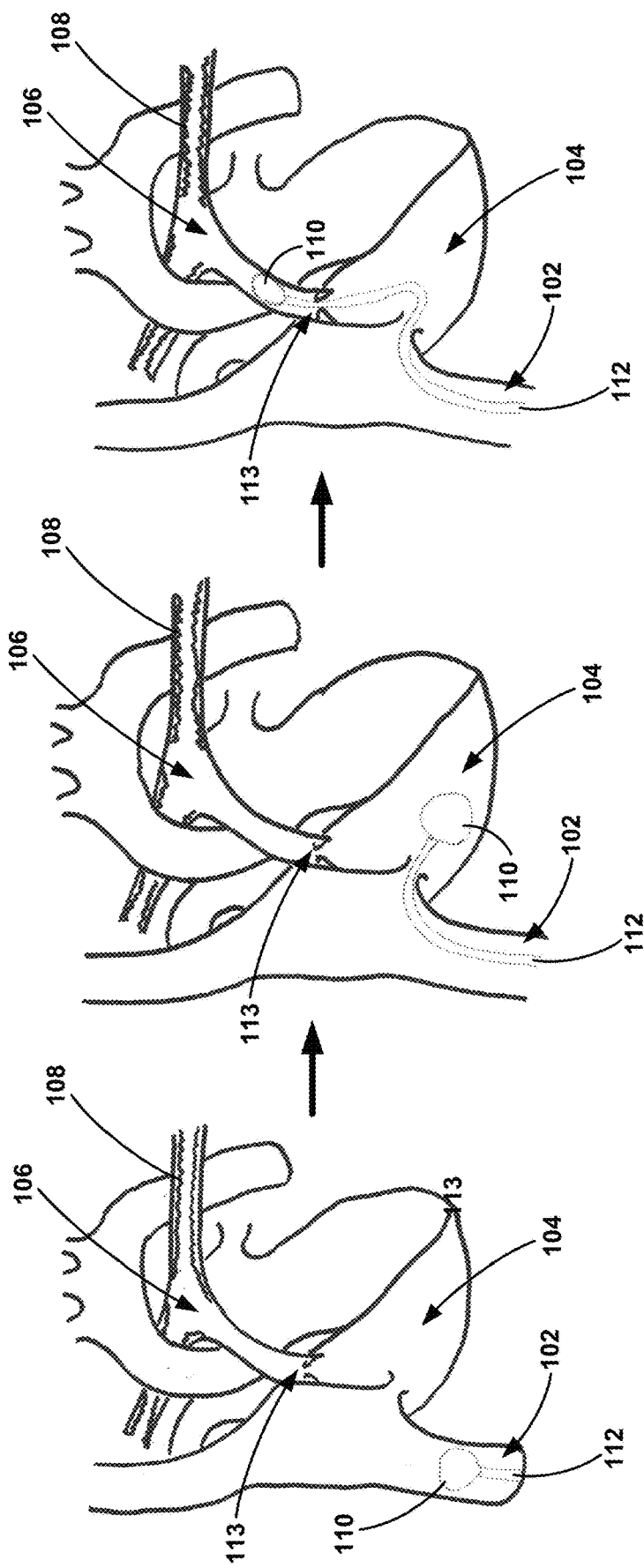
FIG. 1B illustrates the cardiopulmonary structure of FIG. 1A with a sail balloon coupled to the distal end of the first catheter.

With reference to the Figures, FIG. 1A illustrates a schematic of the cardiopulmonary structure, including a heart, and blood flow through the inferior vena cava (IVC) 102, right ventricle (RV) 104, and pulmonary artery (PA) 106 with emboli 108 occluding the pulmonary artery 106. FIG. 1B illustrates an example embodiment including a balloon 110 coupled to the distal end of an apparatus 112. As shown in FIG. 1B, the balloon 110 may be advanced manually or pulled through the inferior vena cava by a balloon 102 via blood flow. In one example, such a balloon 110 may be a sail balloon. The balloon 110 may be coupled to the distal end of the apparatus 112. In operation, this arrangement may permit the balloon to be advanced (e.g., floated) by blood flow and thereby advance the apparatus 112. Once the balloon 110 has entered the inferior vena cava 102, the balloon 110 may then continue through the tricuspid valve and into the right ventricle 104. Finally, the balloon 110 may be advanced through the pulmonary valve 113 along with the apparatus 112. The operator may observe the advancement on a fluoroscopic image and may stop advancement once the apparatus is disposed within the embolism.

Figure 2A:
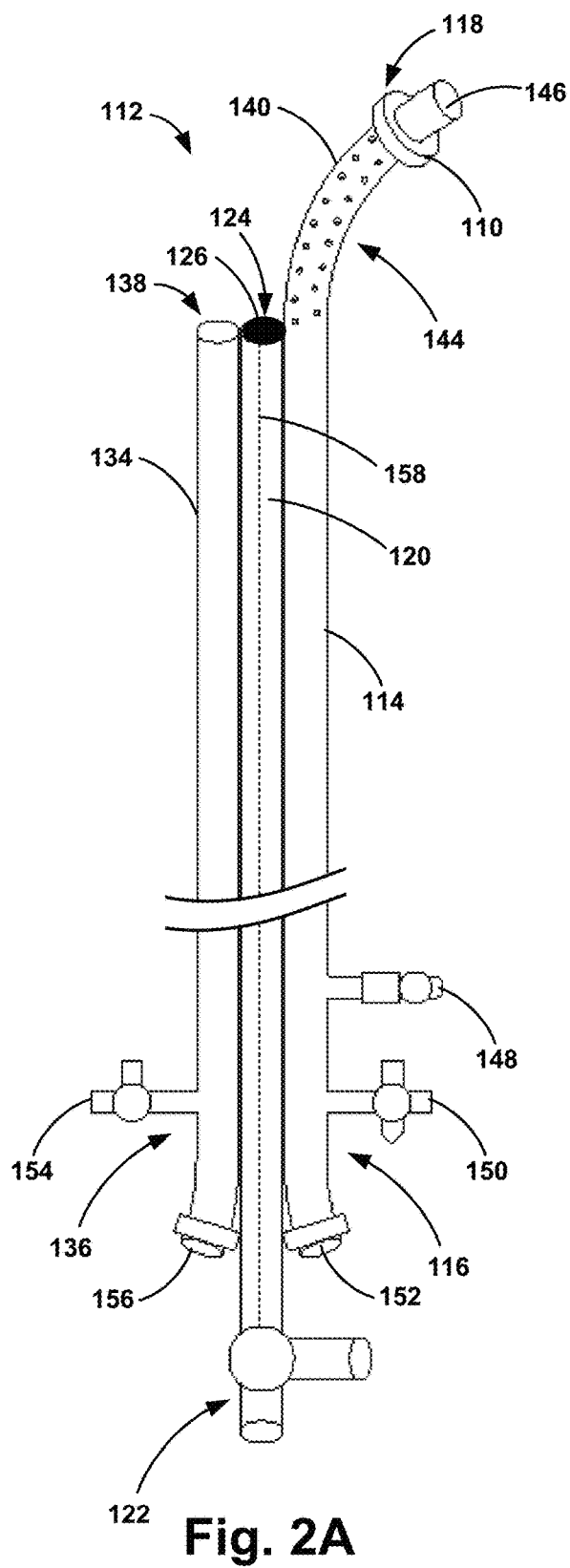
FIG. 2A illustrates an example apparatus in a first position, in accordance with one embodiment of the invention.
Figure 2B:
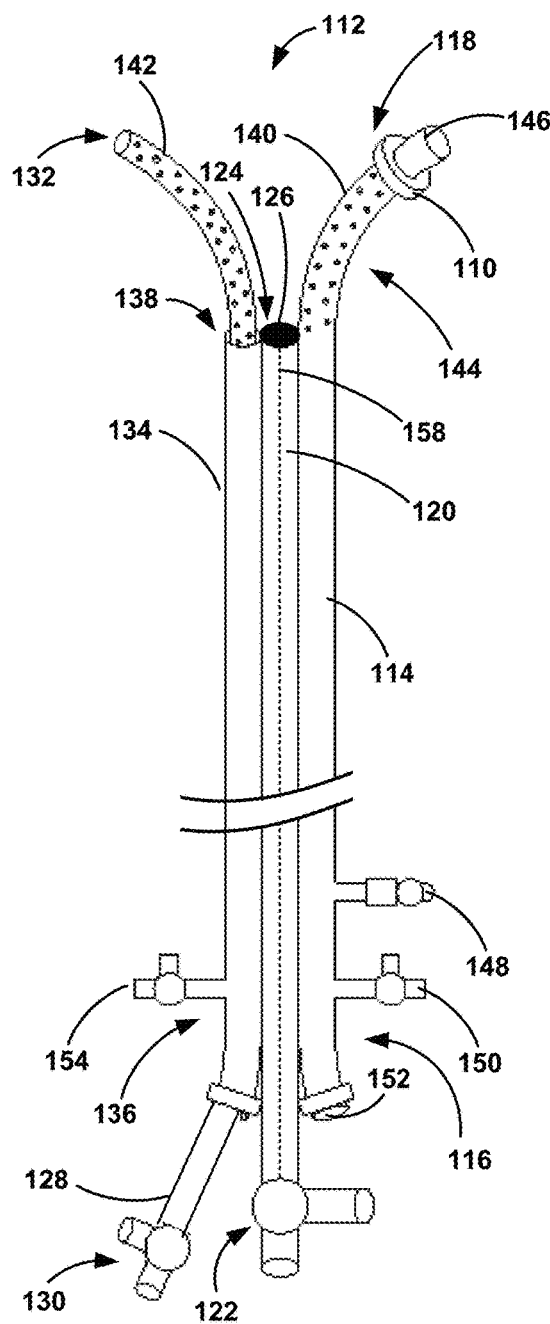
FIG. 2B illustrates the example apparatus of FIG. 2A in a second position, in accordance with one embodiment of the invention.

FIGS. 2A-2B illustrate one example embodiment of an apparatus 112. In some embodiments, the total length of the apparatus 112 may range from about 50 cm to about 500 cm, and preferably from about 50 cm to about 300 cm. As shown in FIGS. 2A-2B, the apparatus 112 may include a first catheter 114 having a proximal end 116 and a distal end 118, a first tubular housing 120 having a proximal end 122 and a distal end 124, one or more pressure sensors 126 coupled to the distal end 124 of the first tubular housing 120, and a second catheter 128 having a proximal end 130 and a distal end 132. As shown in FIGS. 2A-2B, the apparatus 112 may further include a second tubular housing 134 having a proximal end 136 and a distal end 138. The second tubular housing 134 may be coupled to one or more of the first catheter 114 and the first tubular housing 120.

As shown in FIGS. 2A-2B, at least a portion of the distal end 118 of the first catheter 114 includes at least one first outlet 140. The first tubular housing 120 may be coupled to the first catheter 114 proximal to the at least one first outlet 140. Similarly, the second tubular housing may be arranged proximal to the at least one first outlet 140. Further, at least a portion of the distal end 132 of the second catheter 128 includes at least one second outlet 142. In one example, the at least one first outlet 140 may be defined along a section of the first catheter 114 having a length ranging from about 3 cm to about 40 cm, and the at least one second outlet 142 are defined along a section of the second catheter 128 having a length ranging from about 3 cm to about 40 cm. The first and second outlets 140, 142 may be configured to enable a treatment solution to pass through the first and second outlets 140, 142 and into the treatment zone to help dissolve the embolism 108. Further, the first catheter 114 may have an inner diameter in the range of about 3 French to about 15 French, and the second catheter 116 may have an inner diameter in the range of about 1.5 French to about 9 French. Other embodiments are possible as well.

As shown in FIGS. 2A-2B, the distal end 118 of the first catheter 114 may include a curved section 144 having a radius in the range of about 3 cm to about 500 cm. The curved section 144 of the first catheter 114 may help position the distal end 118 of the first catheter 114 into a first branch of the pulmonary artery 106. In one embodiment, the distance between the distal end 118 of the first catheter 114 and the distal end 124 of the first tubular housing 120 may range from about 3 cm to about 40 cm. In addition, the distal end 124 of the first tubular housing 120 may be positioned on the outer curvature of the first catheter 114. The outer curvature of the first catheter 114 may also provide a surface by which to push off of when advancing the second catheter 128 into a second branch of the pulmonary artery 106.

Further, the apparatus 112 may further include a balloon 110 coupled to the distal end 118 of the first catheter 114. The distal end 118 of the first catheter 114 may include a first fluid tight valve 146 configured to direct treatment solution through the at least one first outlet 140 during operation instead of through the distal end 118 of the first catheter 114. The proximal end 116 of the first catheter 114 may further include a lockable balloon inflation port 148, a first infusion stop-cock 150, and a second fluid tight valve 152. The lockable balloon inflation port 148 may be used to inflate and deflate the balloon 110. The first infusion stop-cock 150 may be used to control the flow of the treatment solution through the first catheter 114. The second fluid tight valve 152 may be used to receive a guide wire to direct the apparatus 112 and first catheter 114 to the target vessel. The second tubular housing 134 may be configured to receive the second catheter 128, and the proximal end 136 of the second tubular housing 134 may include a second infusion stop-cock 154 and a third fluid tight valve 156. The second infusion stop-cock 154 may be used to control the flow of the treatment solution through the second catheter 128.

Further, a pressure transducer line 158 may be positioned within the first tubular housing 120, and the one or more pressure sensors 126 may be coupled to the pressure transducer line 158. The pressure transducer line 158 may connect the pressure sensor(s) 126 to a power source and/or a computing device configured to display data from the pressure sensor(s) 126. The pressure sensor(s) 126 may be positioned in a variety of locations. In one example, as shown in FIGS. 2A-2B, the pressure sensor(s) 126 may be positioned at the distal end 124 of the first tubular housing 120. In another example, the pressure sensor(s) 126 may extend beyond the distal end 124 of the first tubular housing 120 and into the pulmonary artery 106. Other locations for the pressure sensor(s) are contemplated as well. As such, the pressure sensor(s) 126 may be advantageously monitored and to observe pulmonary artery pressure within a tolerance thereby indicating treatment completion. Pulmonary artery pressure may become elevated during some cases of pulmonary obstruction and may be a good indicator of hemodynamic stability and hence, treatment completion or lack thereof. Normal pulmonary artery pressures would indicate treatment completion.

As shown in FIG. 2A, in a pre-deployment state, the second catheter 128 may not be positioned in the second tubular housing 134. Further, the second catheter 128 may be moveable between a first position (e.g., a deployment position) and a second position (e.g., a drug delivery position shown in FIG. 2B). For example, the first position may be used during advancement to or placement of the second catheter 128 at the treatment zone, while the second position may be used for infusion of treatment solution through the at least one first outlet 140 of the first catheter 114 and the at least one second outlet 142 of the second catheter 128. The distal end 132 of the second catheter 128 may be positioned substantially within the second tubular housing 134 in the first position (see FIG. 2A), and the distal end 132 of the second catheter 128 may extend through an opening in the distal end 138 of the second tubular housing 134 in the second position (see FIG. 2B). Once the second catheter 128 has been moved into the second position, the treatment solution may then be advanced through the first and second catheters 114, 128 and infused through the first and second one or more outlets 140, 142 into the treatment zone. Each of the one or more outlets 140, 142 may include a hemostatic valve that may allow the treatment solution to pass out through the first and second outlets 140, 142, but minimize back flow of blood into the first and second catheters 114, 128. Such an embodiment may prevent blood from entering the first and second outlets 140, 142 and clotting over time, thereby maintaining the infusing ability of the first and second catheters 114, 128. As the multiple emboli are lysed (i.e., dissolved) via the treatment solution, normal blood flow through the pulmonary arteries 106 may be reestablished and may reduce pulmonary artery pressure and increase systemic arterial pressure bringing the patient back to hemodynamic stability.

Figure 2C:
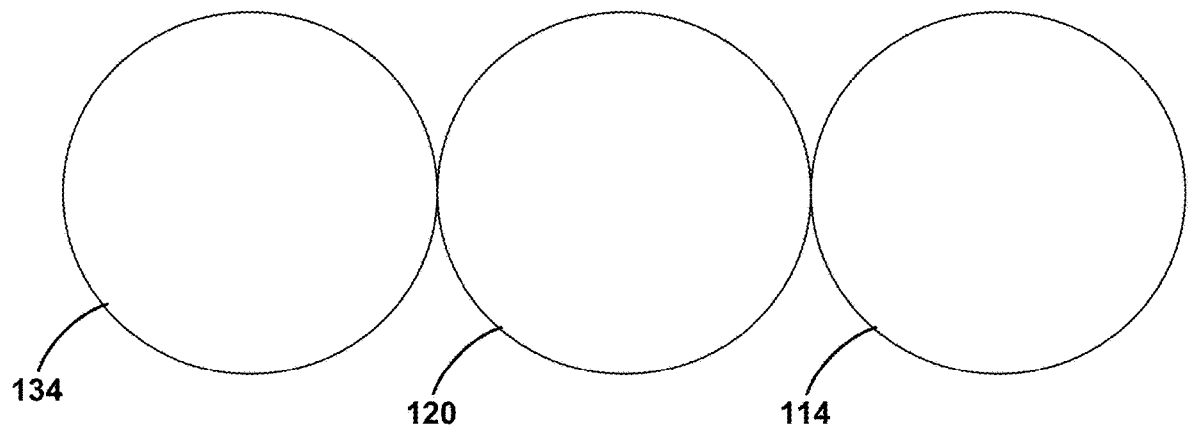
FIG. 2C illustrates a cross-section of one example configuration of the apparatus of FIG. 2A, according to one embodiment.
Figure 2D:
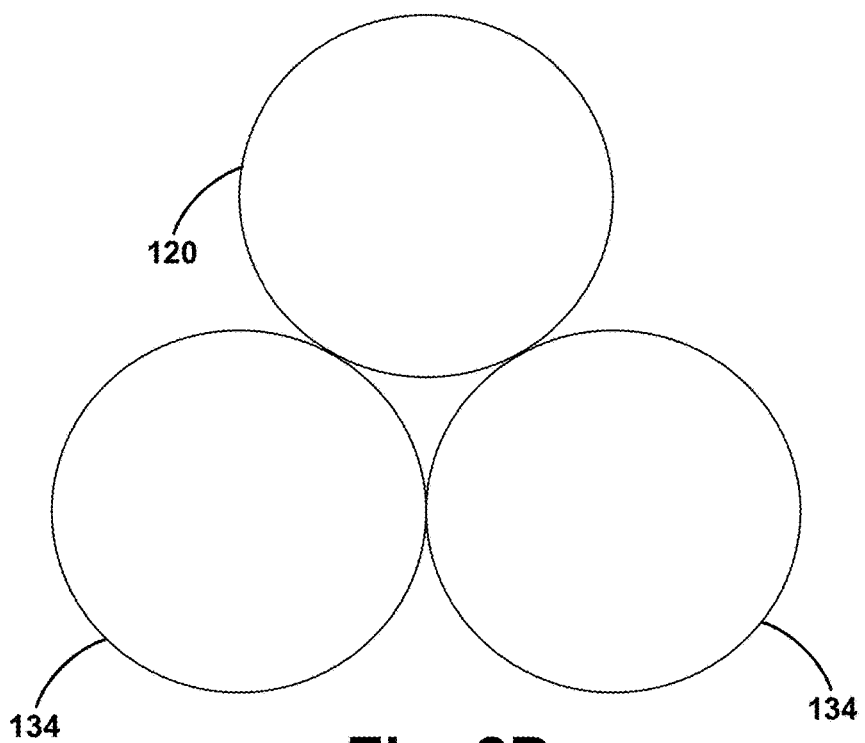
FIG. 2D illustrates a cross-section of another example configuration of the apparatus of FIG. 2A, according to one embodiment.

The arrangement of the first catheter 114, the first tubular housing 120, and the second tubular housing 134 may take various forms. FIG. 2C illustrates a cross-section of the apparatus 114, according to one embodiment. As shown in FIG. 2C, the first catheter 114, the first tubular housing 120, and the second tubular housing 134 may be positioned in a substantially side-by-side configuration. FIG. 2D illustrates a cross-section of the apparatus 114, according to another embodiment. As shown in FIG. 2D, the first catheter 114, the first tubular housing 120, and the second tubular housing 134 may be positioned in a triangular configuration, thereby reducing the overall width of the apparatus 114. Other arrangements are possible as well.

In operation, the apparatus 112 may be positioned in the treatment zone via the balloon 110, or via some other means. In particular, the first catheter 114 may be positioned within a first branch of the pulmonary artery 106. The curved section 144 of the first catheter 114 may aid in positioning the distal end 118 of the first catheter 114 into a first branch of the pulmonary artery 106. The second catheter 128 may then be advantageously directed through the second tubular housing 134, via a guide wire for example, and into a second branch of the pulmonary artery 106. In one example, the apparatus 112 includes an anchoring mechanism configured to anchor the apparatus 112 to a desired vasculature. Such an anchoring mechanism may be coupled to one or more of the first tubular housing 120, the second tubular housing 134, the first catheter 114, and the second catheter 128. In one example, such an anchoring mechanism may include a spring-loaded mechanism to expand the given catheter or tubular housing so as to hold the apparatus 112 in place in the desired vasculature. In another example, the anchoring mechanism comprises a cork screw mechanism configured to puncture the desired vasculature as a means of holding the apparatus 112 in place in the desired vasculature. Other examples are possible as well.

Once positioned in the desired vasculature, the treatment solution may then be infused through the first and second outlets 140, 142 of the first and second catheters 114, 128, respectively, into the treatment zone, as discussed above. The apparatus 112 may further include one or more pressure sensors 126 coupled to the distal end 124 of the first tubular housing 120. As discussed above, the pressure sensor(s) 126 may advantageously monitor and observe pulmonary pressure until the pulmonary pressure decreases below a tolerance, thereby indicating treatment completion.

Figure 3:
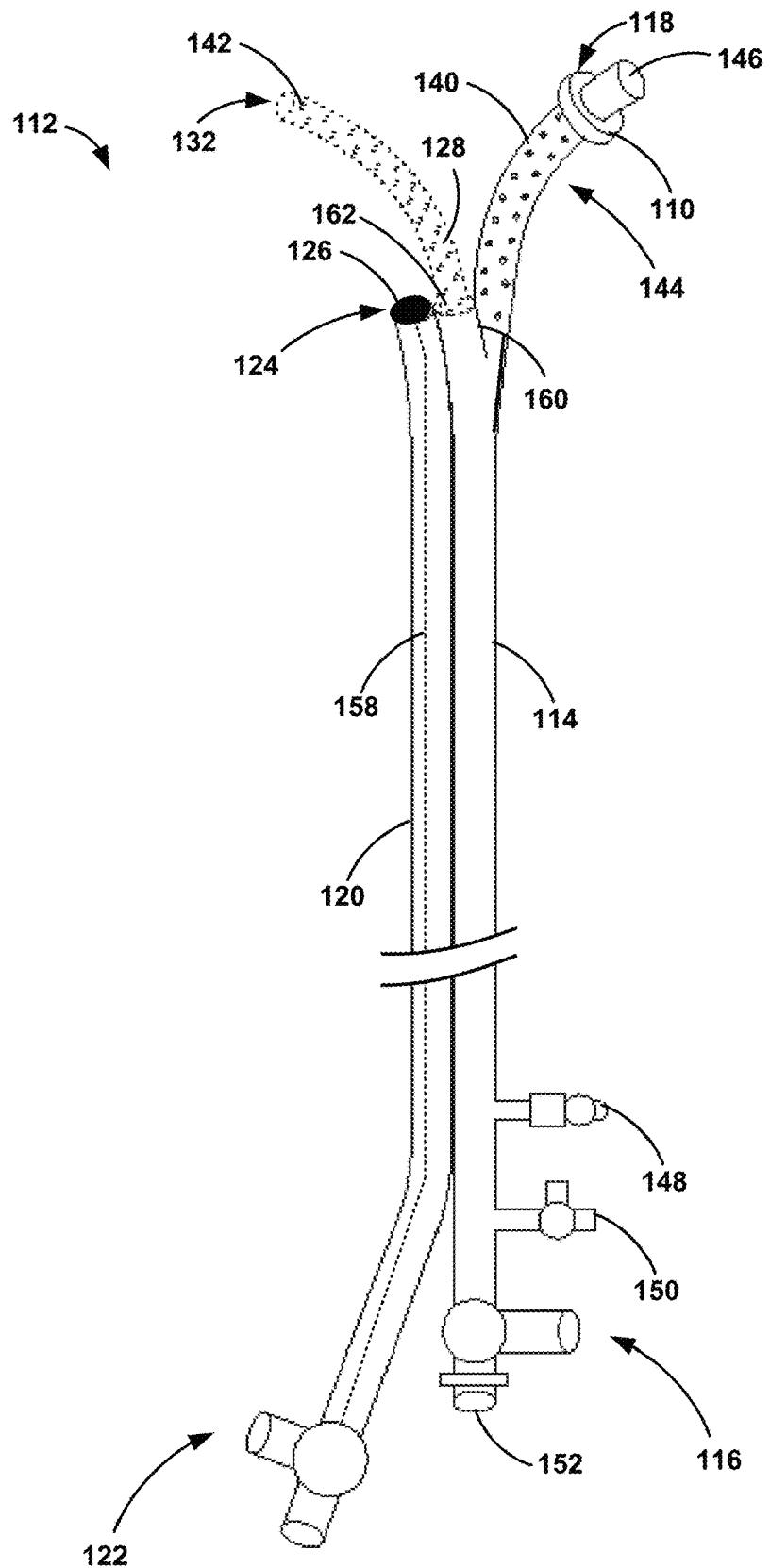
FIG. 3 illustrates another example apparatus, in accordance with one embodiment of the invention.

FIG. 3 illustrates yet another example embodiment of the apparatus 112. As shown in FIG. 3, the apparatus 112 may include a first catheter 114 with at least one first outlet 140, and a second catheter 128 with at least one second outlet 142. The apparatus 112 may further include a first tubular housing 120 coupled to the first catheter 114 proximal to the at least one first outlet 140. The apparatus 112 may further include a catheter diverter 160. The catheter diverter 160 may include a rigid structure coupled to an interior surface of the first catheter 114. As such, the catheter diverter 160 may be configured to at least partially obstruct a lumen of the first catheter 114, such that the second catheter 128 contacts the catheter diverter 160 and is thereby directed through an opening of the first catheter as the second catheter 116 moves from the deployment position to the drug delivery position. In another example, the catheter diverter 160 may be configured to at least partially obstruct a lumen of the first catheter 114, such that a guide wire contacts the catheter diverter 160 and is thereby directed through an opening 162 of the first catheter and toward a second branch of the pulmonary artery 106. Then the second catheter 128 may be directed along the guide wire and through the opening 162 in the first catheter 114 as the second catheter 128 moves from the deployment position to the drug delivery position.

As shown in FIG. 3, the distal end 118 of the first catheter 114 may include a curved section 144 having a radius in the range of about 3 cm to about 500 cm. The curved section 144 of the first catheter 114 may aid in positioning the distal end 118 of the first catheter 114 into a first branch of the pulmonary artery 106. In one embodiment, the distance between the distal end 118 of the first catheter 114 and the side port 162 may range from about 3 cm to about 40 cm such that the opening 162 in the first catheter 114 is arranged between the distal end 1118 and the proximal end 116 of the first catheter 114. In one example, the opening 162 of the first catheter 114 is coupled to a port. The side port 162 may include a fluid tight valve that may be used to receive a guide wire to direct the second catheter 128 to the target vessel. Further, the side port 162 may advantageously aid in directing the second catheter 128 in the direction of the second branch of the pulmonary artery 106.

As shown in FIG. 3, the apparatus 112 may further include a balloon 110 coupled to the distal end 118 of the first catheter 114. The distal end 118 of the first catheter 114 may also include a first fluid tight valve 146 configured to direct treatment solution through the at least one first outlet 140 during operation. The first fluid tight valve 146 will be fluid tight but will allow a guide wire to pass through to direct the first catheter 114 to the target vessel. The proximal end 116 of the first catheter 114 may further include a balloon inflation port 148, a first infusion stop-cock 150, and a second fluid tight valve 152. The balloon inflation port 148 may be used to inflate the balloon 110. The first infusion stop-cock 150 may be used to control the flow of the treatment solution through the first catheter 114. The second fluid tight valve 152 may be used to receive a guide wire to direct the first catheter 114 to the target vessel. Further, the proximal end 122 of the first tubular housing 120 may include a pressure transducer line 158, and one or more pressure sensors 126 may be coupled to the pressure transducer line 158, as discussed above.

In a pre-deployment state, the second catheter 128 may not be positioned in the second tubular housing 134. Further, the second catheter 128 may be moveable between a first position (e.g., a deployment position) and a second position (e.g., a drug delivery position shown in FIG. 3). For example, the first position may be used during advancement to or placement of the second catheter 128 at the treatment zone, while the second position may be used for infusion of treatment solution through the at least one first outlet 140 of the first catheter 114 and the at least one second outlet 142 of the second catheter 128. The distal end 132 of the second catheter 128 may be positioned substantially within the first catheter 114 in the first position, and the distal end 132 of the second catheter 128 may extend through an opening 162 in the first catheter 114 in the second position. Once the second catheter 128 has been moved into the second position, the treatment solution may then be advanced through the first and second catheters 114, 128 and infused through the at least first and second outlets 140, 142 into the treatment zone. As discussed above, each of the at least first and second outlets 140, 142 may include a hemostatic valve that will allow the treatment solution to pass out through the at least one first and second outlets 140, 142, but may minimize back flow of blood into the first and second catheters 114, 128. Such an embodiment may minimize blood entering the at least first and second outlets 140, 142 and clotting over time, thereby maintaining the infusing ability of the first and second catheters 114, 128. As the multiple emboli are lysed (i.e., dissolved) via the treatment solution, normal blood flow through the pulmonary arteries 106 may be reestablished and may reduce pulmonary artery pressure and increase systemic arterial pressure bringing the patient back to hemodynamic stability.

In operation, the apparatus 112 may be positioned in the treatment zone via the balloon 110, or via some other means. In particular, the first catheter 114 may be positioned within a first branch of the pulmonary artery 106. The curved section 144 of the first catheter 114 may aid in positioning the distal end 118 of the first catheter 114 into a first branch of the pulmonary artery 106. The second catheter 128 may then be advantageously directed, via a guide wire for example, through the first catheter 114, out the opening 162, and into a second branch of the pulmonary artery 106. The treatment solution may then be infused through the at least one first and second outlets 140, 142 of the first and second catheters 114, 128, respectively, into the treatment zone, as discussed above. The apparatus 112 may further include one or more pressure sensors 126 coupled to the distal end 124 of the first tubular housing 120. As discussed above, the pressure sensor(s) 126 may advantageously monitor and observe pulmonary pressure until the pulmonary pressure decreases below a tolerance thereby indicating treatment completion and a return to hemodynamic stability.

Figure 4A:
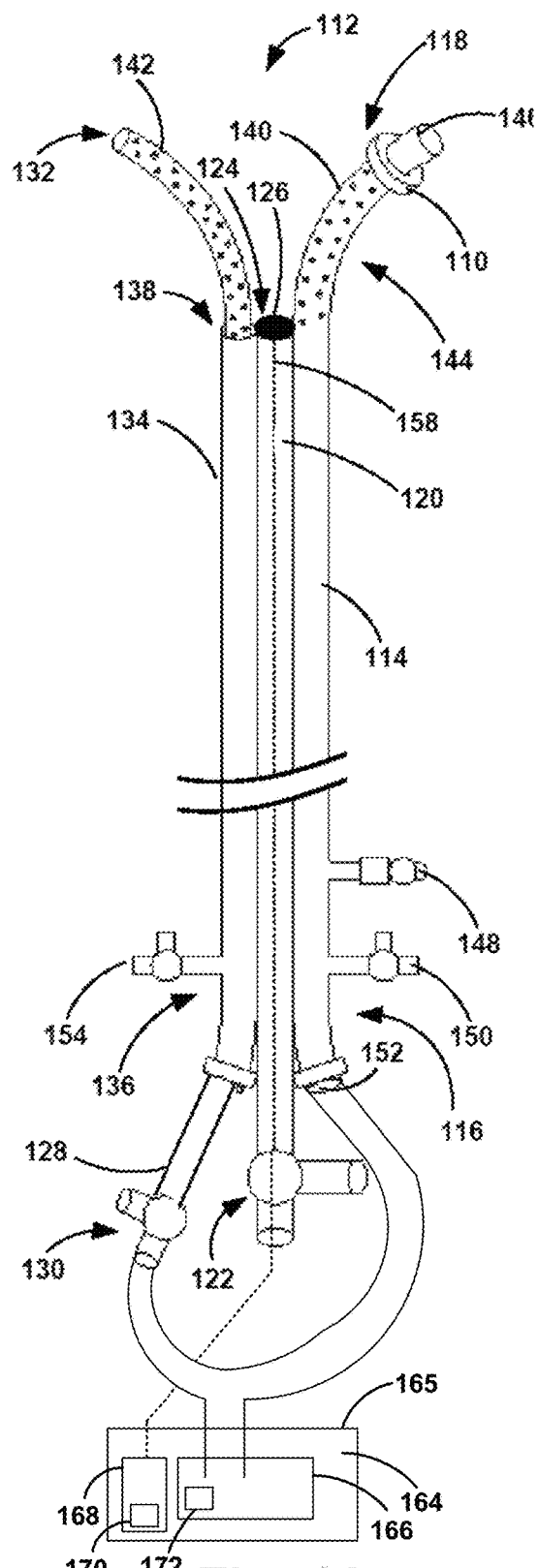
FIG. 4A illustrates the example apparatus of FIG. 2B including a pump, in accordance with one embodiment of the invention.
Figure 4B:
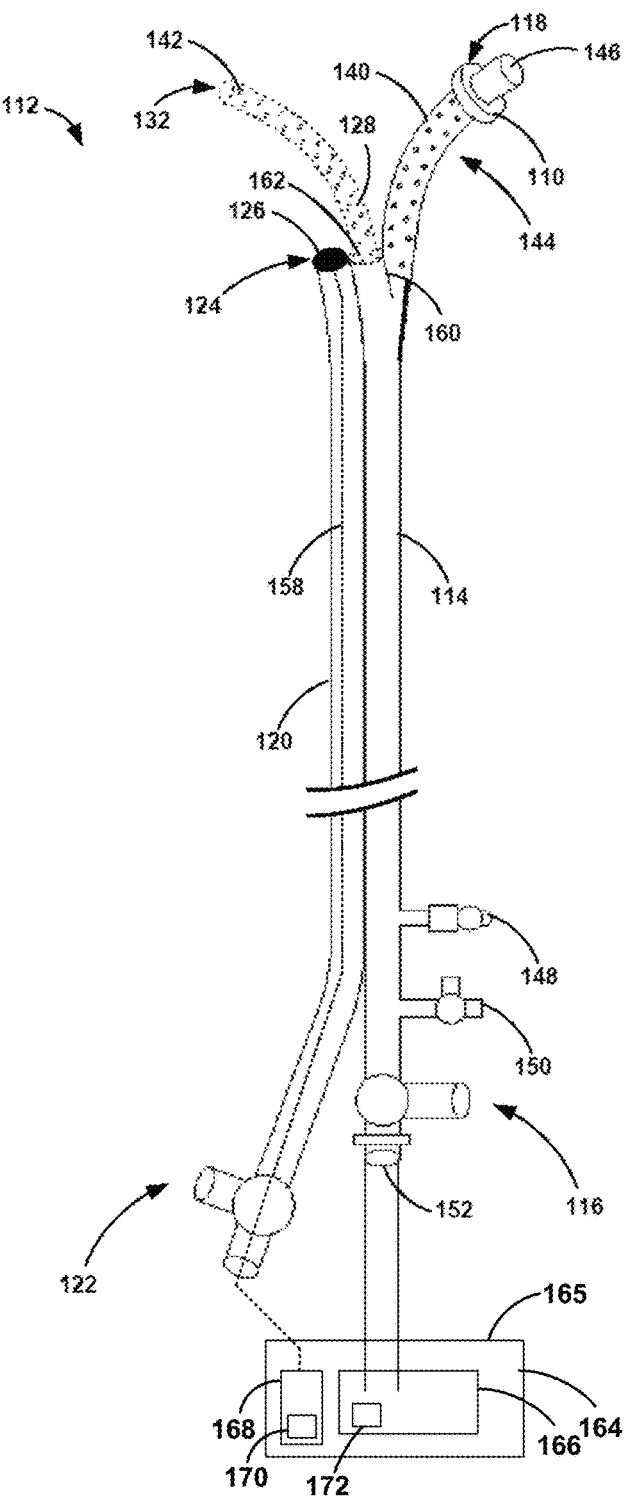
FIG. 4B illustrates the example apparatus of FIG. 3 including a pump, in accordance with one embodiment of the invention.

FIG. 4A illustrates the example apparatus 112 of FIG. 2B including a pump 164, in accordance with one embodiment of the invention. Similarly, FIG. 4B illustrates the example apparatus of FIG. 3 including the pump 164, in accordance with another embodiment of the invention. As shown in FIGS. 4A and 4B, the pump 164 may be coupled to at least one of the first catheter 114 and the second catheter 128. In particular, the pump 164 may be configured for fluid communication with the first catheter 114 and/or the second catheter 128. The apparatus 112 may further include a reservoir 166 coupled to the pump 164. As shown in FIGS. 4A and 4B, the reservoir 166 may be positioned within a housing 165 of the pump 164. The reservoir 166 may be configured to hold a treatment solution for delivery to the pulmonary artery via the pump 164. Treatment solutions that are of interest for the pulmonary arteries include vasodilators including epoprostenol (Flolan) and iloprost (Ventavis) and endothelin receptor antagonists such as Ambrisentan (Letairis). Additional therapeutic solutions that can be infused into the pulmonary arteries include Sildenafil (Viagra) and Tadalafil (Cialis), high-dose calcium channel blockers including Amlodipine (Norvasc), Diltiazem (Cardizem, Tiazac), and Nifedipine (Adalat, Procardia), and various diuretics. Various nitrates for coronary artery disease may also be beneficial when infused, including isosorbide dinitrate (Dilatrate, Isordil), isosorbide mononitrate (ISMO), and nitroglycerine (Nitro-Dur, Nitrolingual, and Nitrostate). Therapeutics that may be infused with the present invention for treating heart failure include inotropes such as dabutamine, angiotensin-convertine enzyme inhibitors, angiotensin II receptor blockers, beta blockers, diuretics, aldosterone antagonists, and digoxin.

In such an example, the apparatus 112, pump 164, and reservoir 166 may be implantable within the patient. In particular, the pump 164 and reservoir 166 may be positioned subcutaneously in a pocket between the skin and the muscle of the patient or in or beneath a fat pocket of the patient, for example. In example embodiments, the pump 164 and reservoir 166 may be positioned in the abdomen, buttock or thigh of the patient. Other example locations are possible as well. The pump 164 may include a transcutaneously accessible reservoir 166 for refilling the treatment solution. This may be done via palpable transcutaneous markers and ultrasound- or fluoroscopic-guidance when the patient is seen for follow-up.

In operation, the apparatus 112 may be positioned in the treatment zone via the balloon 110, or via some other means. In particular, the first catheter 114 may be positioned within a first branch of the pulmonary artery 106. The curved section 144 of the first catheter 114 may aid in positioning the distal end 118 of the first catheter 114 into a first branch of the pulmonary artery 106. The second catheter 128 may then be advantageously directed, via a guide wire for example, through the first catheter 114, out the opening 162, and into a second branch of the pulmonary artery 106. The apparatus 112 will remain in the branch of the pulmonary artery and disposed through the right atrium and right ventricle of the heart when the pump 164 is subcutaneously implanted. The pump 164 may then be positioned in the patient and subsequently coupled to at least one of the first catheter 114 and the second catheter 128, as discussed above. The first and second catheters 114, 128 may be coupled to the pump 164 or pumps via a press fit friction connection with an external locking ring, among other options for attachment. The one or more pressure sensors 126 will be in electronic communication with the pump 164, so the one or more sensors 126 will be conductively coupled to the pump 164. The apparatus 112 may further include one or more pressure sensors 126 coupled to the distal end 124 of the first tubular housing 120.

Further, the apparatus 112 may include a controller 168 coupled to the pump 164. As shown in FIGS. 4A and 4B, the controller 168 may be coupled to the one or more sensors 126 via the pressure transducer line 158. In such an embodiment, the one or more pressure sensors 126 will communicate with the pump 164 so that the controller 168 may register the pressures sensed by the one or more sensors 126. In particular, the controller 168 may include a wireless communication interface 170 that transmits information received from the one or more sensors 126, along with other information, to a computing device. Thus, the controller 168 may be configured to (i) determine if, via the one or more pressure sensors 126, a pulmonary artery blood pressure is greater than a threshold value, and (ii) in response to the determination that the pulmonary artery blood pressure is greater than the threshold value, activate the pump 164 to advance the treatment solution from the reservoir 166 to the at least one first outlet 140 of the first catheter 114 and the at least one second outlet 142 of the second catheter 128. The pump 164 may also include a sensor 172 for determining the level of the therapeutic solution remaining in the reservoir 166. The sensor 172 may be in communication with the controller 168, and the wireless communication interface 170 may be configured to transmit the determined volume to a computing device, such as a physician's computer. The physician may therefore monitor when the treatment solution is almost empty, and may contact the patient to schedule a time to refill the reservoir 166.

Further, the controller may be configured to (i) determine, via the one or more pressure sensors 126, a blood pressure is less than the threshold value, and (ii) in response to the determination that the blood pressure is less than the threshold value, either modulate the flow rate accordingly or deactivate the pump 164. In one particular example, the apparatus 112 may include a first pump coupled to the first catheter 114, and a second pump coupled to the second catheter 128. In such an example, the controller 168 may be configured to activate and deactivate the first and second pumps independently of one another. Further, in such an example the apparatus 112 may include a first reservoir coupled to the first pump, and a second reservoir coupled to the second pump. The first and second reservoirs may contain the same treatment solution, or the treatment solution in the first reservoir may be different than the treatment solution in the second reservoir. When there are two or more reservoirs, the access site for each reservoir may include clearly discernible markers for the purposes of refilling so that the wrong medication is not added to the wrong reservoir. For example, each of the first reservoir and the second reservoir may include a unique identifier such as a stamp or a radiopaque marker. In another example, the unique identifier may be a shape of the first reservoir and the second reservoir, such that the first reservoir has a different shape than the second reservoir. In another example, each reservoir may include a unique coupling mechanism to a corresponding catheter. Other examples are possible as well.

In one example, the one or more pressure sensors 126, the sensor 172, and/or pump 164 may be operated periodically in order to save power and extend battery life. For instance, if a treatment solution has a long acting characteristic, the pump 164 could be programmed to turn on only after the treatment solution is believed to be fully metabolized or become inactive. Additionally, heart failure episodes develop over a relatively long period of time, up to 60 days, with gradually increasing pulmonary artery pressure along the way, so the sensor 172 could be turned on in a delayed frequency which allows for conservation of the battery. The sensor 172 could be constructed as a micro-electromechanical system so that it may be remotely charged with radio frequency methods. Alternatively, the pump 164 may be charged using energy harvesting methodologies wherein a flexible integrated device may be laid on an organ such as the heart or lungs in order to harvest the mechanical energy for charging the battery on the sensor 172 or the pump 164. The pump 164 may be made by layering piezoelectric material such as lead zirconate titanate onto flexible silicone with added rectifiers and batteries, in one example.

Further, the pump 164 may be biocompatible and blood compatible. Proper hermetic encapsulation is required to protect the electronics from water intrusion that can result in sensor drift and device failure. Hermetic encapsulation is also required to prevent the ingress of oxygen which may oxidize metal connections such as solders and lead to attachment failure. The sensor 172 may also manage the immune response occurring at the surface to prevent fibrous tissue encapsulation or other cellular or blood-based biofouling. The one or more pressure sensors 126 may be made from a membrane and a sealed cavity. With one membrane element responding to and deflecting under pressure and the other membrane being placed on the bottom rigid surface within the vacuum sealed cavity. Deflection of the membrane may cause changes in the capacitance measured between the electrode pair. Alternatively, piezoresistive sensing may allow for a piezoresistor to be patterned onto the membrane surface, and deflection of the membrane may be transduced into a change in resistance, usually measured via a bridge circuit. The membrane exposed to blood may be designed with surface properties to resist protein adsorption and ultimately biofouling. Other embodiments are possible as well.

As such, the apparatus 112 shown in FIG. 4A may be used to treat pulmonary hypertension or heart failure of a patient. Pulmonary hypertension begins when tiny arteries in the lungs, called pulmonary arteries, and capillaries become narrowed, blocked, or destroyed. This makes it harder for blood to flow through your lungs, and raises pressure within your lungs' arteries. Ordinarily, the blood flows easily through the vessels in your lungs, so blood pressure is usually much lower in your lungs. With pulmonary hypertension, the rise in blood pressure may be caused by changes in the cells that line your pulmonary arteries. These changes may cause extra tissue to form, eventually narrowing or completely blocking the blood vessels, making the arteries stiff and narrow. This may impede blood to flow, thereby raising the blood pressure in the pulmonary arteries.

Thus, the treatment solution may take various forms to help treat pulmonary hypertension. Endothelins are peptides that constrict blood vessels and raise blood pressure. Overproduction of endothelin in the lungs may cause pulmonary hypertension, which may sometimes be treated with endothelin receptor antagonists, such as bosentan, sitaxentan, or ambrisentan. Inhaled epoprostenol may reduce pulmonary pressure through vasodilation. A dose of 60 micrograms is hemodynamically safe and typically completely reverses after 25 minutes. In one embodiment, less than 60 micrograms of the endothelin receptor antagonist can be released from the pump 164, through the first and second catheters 114, 128, and into the pulmonary vasculature reducing the pulmonary artery pressure. Once the pulmonary artery pressure is reduced below the threshold value, delivery of the drug may cease. The effects will likely reverse in about 25 minutes. If pulmonary artery pressure again increases after the drug reverses, the pump 164 may release more treatment solution from the reservoir 166. Several therapeutic drugs can be used with the pump 164 and apparatus 112, and this application should not be limited to endothelin receptor antagonists. An alternative drug that could be used is Ventavis. Ventavis is traditionally inhaled every three hours. In this alternative embodiment, when pulmonary artery pressure increases above the threshold value, the Ventavis may be released effectively reducing the pulmonary artery pressure. Other treatment solutions for treating pulmonary hypertension are possible as well.

Further, the treatment solution may take various forms to help treat heart failure. Angiotensin-converting enzyme (ACE) inhibitors are a vasodilator, a drug that widens blood vessels to lower blood pressure, improve blood flow and decrease the workload on the heart. Examples include enalapril (Vasotec), lisinopril (Zestril) and captopril (Capoten). Angiotensin II receptor blockers are drugs, which include losartan (Cozaar) and valsartan (Diovan), have many of the same benefits as ACE inhibitors. They may be an alternative for people who can't tolerate ACE inhibitors. Beta blockers are a class of drugs that slow heart rate and reduce blood pressure and also limits or reverses some of the damage to the heart in the event of systolic heart failure. Examples include carvedilol (Coreg), metoprolol (Lopressor) and bisoprolol (Zebeta). These medicines reduce the risk of some abnormal heart rhythms and lessen the chance of dying unexpectedly. Beta blockers may reduce signs and symptoms of heart failure, improve heart function, and increase longevity. Diuretics are drugs that cause frequent urination and keep fluid from collecting in the body. Diuretics, such as furosemide (Lasix), may also decrease fluid in the lungs to ease breathing. Aldosterone antagonists are drugs that include spironolactone (Aldactone) and eplerenone (Inspra). These are potassium-sparing diuretics, which may also have additional properties that may help people with severe systolic heart failure live longer. Inotropes are intravenous medications used in people with severe heart failure in the hospital to improve heart pumping function and maintain blood pressure. Digoxin (Lanoxin), also referred to as digitalis, is a drug that increases the strength of the heart muscle contractions. It also tends to slow the heartbeat. Digoxin reduces heart failure symptoms in systolic heart failure and typically may be given to someone with a heart rhythm problem, such as atrial fibrillation. Other treatment solutions for treating heart failure are possible as well.

Figure 5:
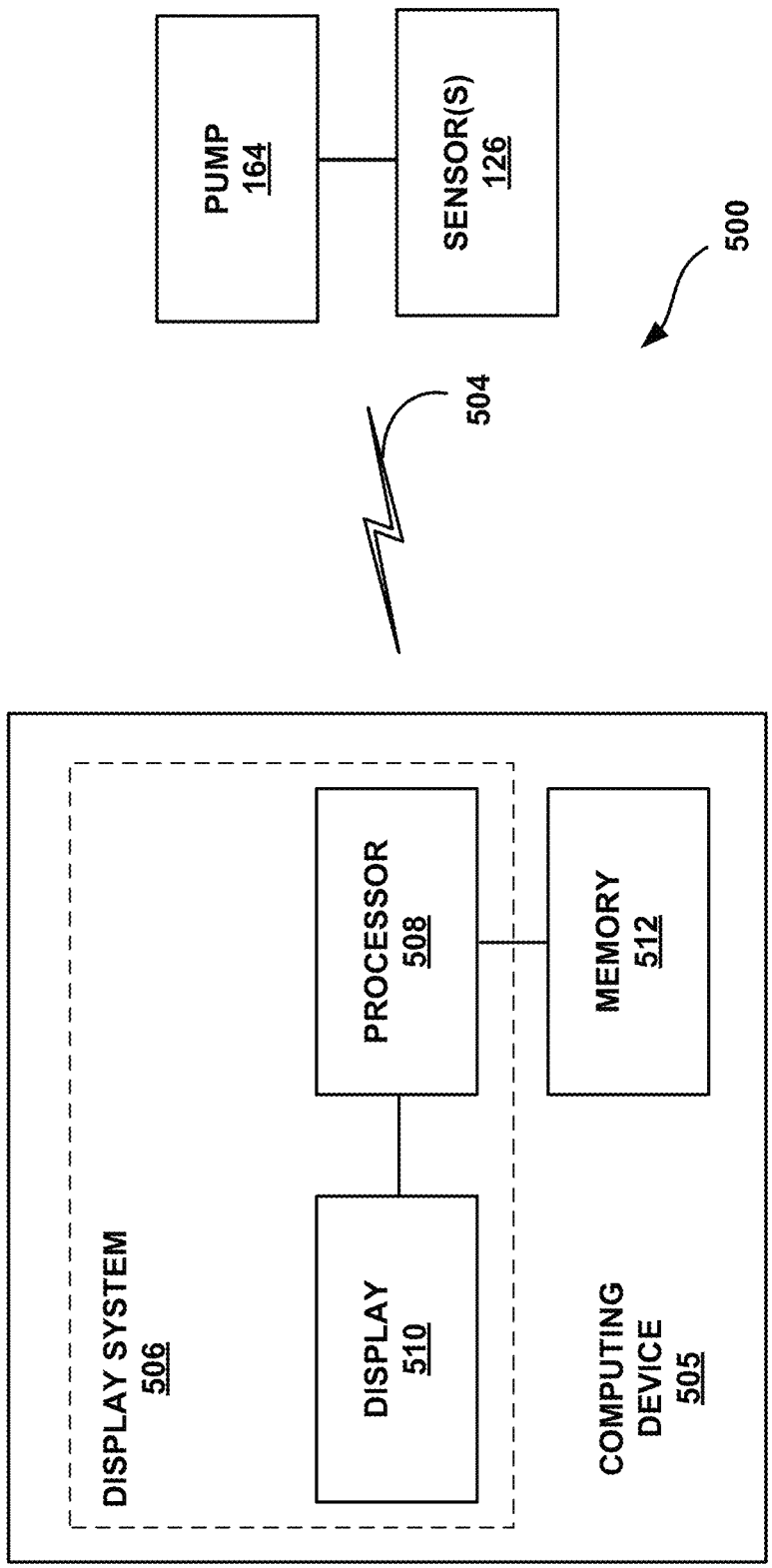
FIG. 5 is a schematic drawing of a computer network infrastructure, in accordance with one embodiment of the invention.

FIG. 5 illustrates an example schematic drawing of a computer network infrastructure. In one system 500, a computing device 502 communicates with the pump 164 using a communication link 504, such as a wired or wireless connection. The computing device 502 may be any type of device that may receive data and display information corresponding to or associated with the data. For example, the computing device 502 may be a mobile phone, a tablet, or a personal computer as examples.

Thus, the computing device 502 may include a display system 506 comprising a processor 508 and a display 510. The display 510 may be, for example, an optical see-through display, an optical see-around display, or a video see-through display. The processor 508 may receive data from the pump 164, and configure the data for display on the display 510. In another embodiment, the processor 508 may receive data from the one or more sensors 126, and configure the data for display on the display 510. Depending on the desired configuration, processor 508 can be any type of processor including, but not limited to, a microprocessor, a microcontroller, a digital signal processor, or any combination thereof.

The computing device 502 may further include on-board data storage, such as memory 512 coupled to the processor 508. The memory 512 may store software that can be accessed and executed by the processor 508, for example. The memory 512 can include any type of memory now known or later developed including but not limited to volatile memory (such as RAM), non-volatile memory (such as ROM, flash memory, etc.) or any combination thereof.

According to an example embodiment, the computing device 502 may include program instructions that are stored in the memory 512 (and/or possibly in another data-storage medium) and executable by the processor 508 to facilitate the various functions described herein. Although various components of the system 500 are shown as distributed components, it should be understood that any of such components may be physically integrated and/or distributed according to the desired configuration of the computing system.

The pump 164 and the computing device 500 may contain hardware to enable the communication link 504, such as processors, transmitters, receivers, antennas, etc.

In FIG. 5, the communication link 504 is illustrated as a wireless connection; however, wired connections may also be used. For example, the communication link 504 may be a wired link via a serial bus such as a universal serial bus or a parallel bus. A wired connection may be a proprietary connection as well. The communication link 504 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. Such a communication link 504 may have a frequency band in the range of 402-405 MHz or greater than 2 GHz.

As such, the pump 164 and or the one or more pressure sensors 126 could have wireless communication capabilities for transmitting data to the patient's physician regarding power consumption, current reservoir levels, remaining power levels, infusion rates, and pressure measurements over time, as discussed below in relation to FIG. 5. Further, such a wireless communication system 500 may be designed such that the microcontroller and non-volatile storage of the pump are not damaged by x-rays, and does not cause dielectric heating during MRI examinations.

In such a computer system 500, the pump 164 will be able to communicate with the computing device 505, and the computing device 505 may register the reservoir's therapeutic solution level as well as the estimated time remaining until a refill is required. The pump 164 may also register and transmit a summary of time-based pulmonary artery pressures in addition to dose responses of the pulmonary artery pressures over a given time period to the computing device 505. The pump 164 will also be able to communicate with the computing device 505 to register the pump battery's remaining power level as well as the current average power consumption rate. The computing device 505 may then transmit this information to the physician remotely to encourage better patient-physician care management. In addition, the pump 164 may wirelessly or remotely gather information such as oxygen saturation, system blood pressure, (actual or relative) and adjust medication output from the pump 164 or pumps by either turning on or off the pump 164. This information may be recorded, stored, and transmitted wirelessly by the pump 164 and/or computing device 505.

It may be clinically useful for patients who have pulmonary hypertension or heart failure to have additional patient information tracked such as blood pressure, heart rate, and oxygen saturation. In one embodiment, a patient who had an implanted pressure sensing catheter 112 and pump 164 would also have a wearable device, such as computing device 505, that could monitor blood pressure, heart rate, and/or oxygen saturation. The computing device 505 could communicate with the pump 164 via wireless communication link 504, and data could be stored either on the pump 164 or on the computing device 505. The information could also be transmitted to the physician periodically or downloaded on the physician's PC when the patient is seen for a follow-up appointment. In such an embodiment, the pump 164 may be controlled with inputs of heart rate, blood pressure, and oxygen saturation in addition to the pulmonary artery pressures as well as the medication infusion rates. In another potential embodiment, the pump 164 may have a safety feature that deactivates the pump 164 if it does not receive the aforementioned inputs. In this scenario, a warning message will be sent to the display 510 of the computing device 505 and/or the patient's physician.

Figure 6:
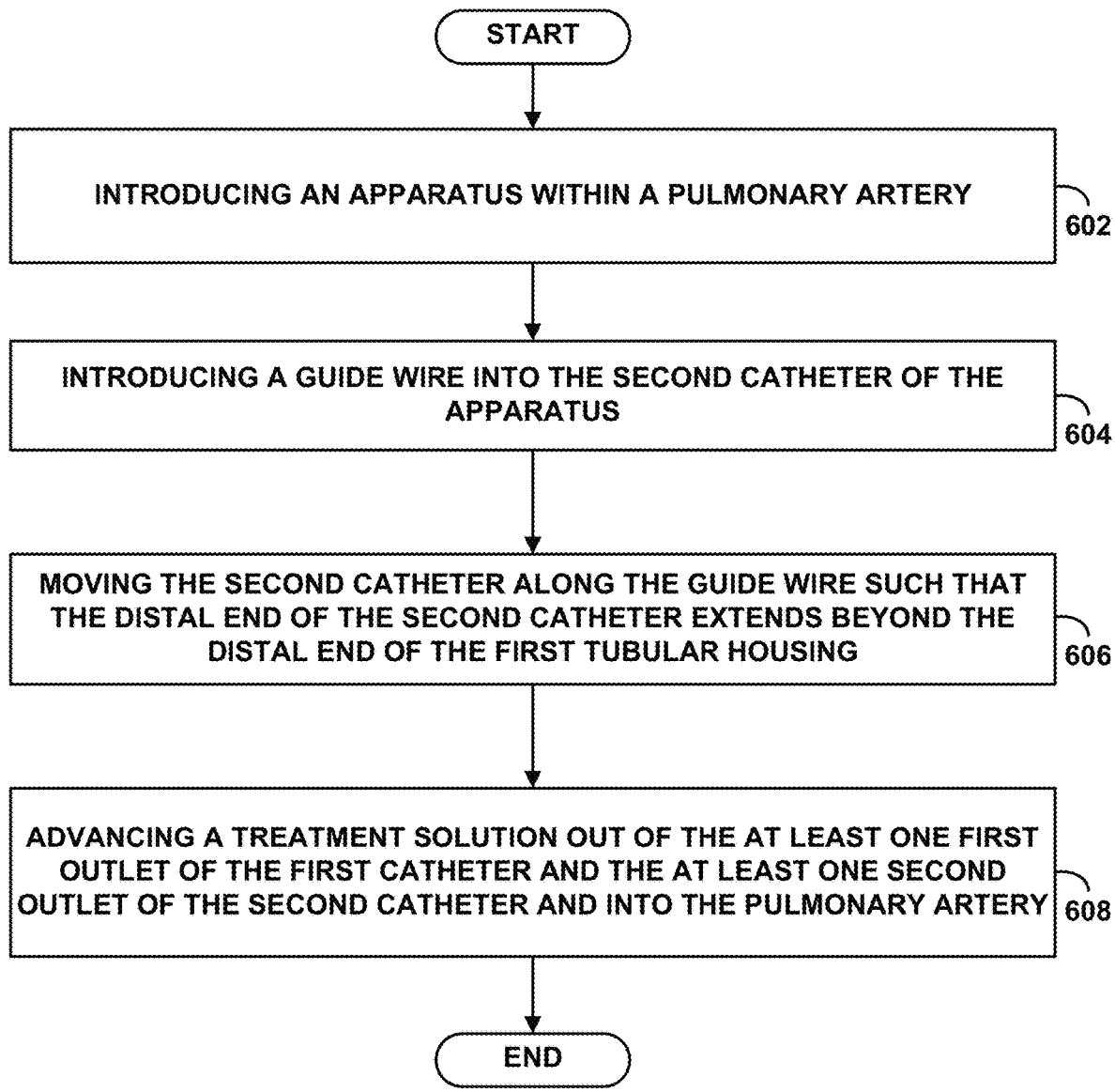
FIG. 6 is a flow chart depicting functions that can be carried out in accordance with example embodiments of the disclosed methods.

FIG. 6 is a simplified flow chart illustrating a method according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 602, the method involves introducing an apparatus within a pulmonary artery. The apparatus may be the apparatus 112, as described above in relation to FIGS. 1A, 1B, 2A, 2B, 3, 4A, 4B, and 5. At block 604, the method involves introducing a guide wire into the second catheter of the apparatus. At block 606, the method involves moving the second catheter along the guide wire such that the distal end of the second catheter extends beyond the distal end of the first tubular housing. At block 608, the method involves advancing a treatment solution out of the first one or more outlets of the first catheter and the second one or more outlets of the second catheter and into the pulmonary artery. In one example, the treatment solution may be advanced through the first catheter and the second catheter at a flow rate in the range of about 5 cc/hr to about 100 cc/hr.

In one embodiment, the method may further include monitoring a blood pressure, via the one or more pressure sensors, after introducing the apparatus within the pulmonary artery. This may permit a user to establish a patient's base line pulmonary artery blood pressure. In a catheter-directed lytic infusion to the pulmonary arteries, the catheter may be left in place for 12-36 hours. If the patient is under monitoring by an ICU nurse, the nurse can monitor the pulmonary artery pressure or the system can have an alarm or infusion control stop when the pulmonary artery pressure reaches a pre-prescribed level. Then, the method involves monitoring the blood pressure, via the one or more pressure sensors, after advancing the treatment solution to the at least one first outlet of the first catheter and to the at least one second outlet of the second catheter. This may permit a user to determine when the treatment solution has reduced or removed a blockage by observing a decrease in pulmonary artery blood pressure. In one embodiment, the blood pressure that is monitored may be a pulmonary artery pressure, for example.

In another example, the method may further include the steps of inflating a balloon coupled to the distal end of the first catheter, and advancing the distal end of the first catheter, via the balloon, from an inferior vena cava to a right ventricle, through a pulmonary valve and within the pulmonary artery. In this embodiment, the inflated balloon may be acted upon by blood flow. In another example, the method may further include the steps of positioning the distal end of the first catheter into a first branch of the pulmonary artery, advancing the distal end of the second catheter through a port of the first catheter, and positioning the distal end of the second catheter into a second branch of the pulmonary artery. In yet another example, the method may further include the steps of positioning the distal end of the first catheter into a first branch of the pulmonary artery, advancing the distal end of the second catheter out of the distal end of the second tubular housing, and positioning the distal end of the second catheter into a second branch of the pulmonary artery.

The method may further include determining a first blood pressure, via the one or more pressure sensors at a first time, determining a second blood pressure, via the one or more pressure sensors at a second time, and comparing the first blood pressure to the second blood pressure to determine a change in blood pressure. This may permit a user to determine when the treatment solution has reduced or removed a blockage by observing a decrease in pulmonary artery blood pressure over time.

In another embodiment, the method further includes determining, via one or more pressure sensors, a blood pressure is less than a threshold value, and responsively removing the apparatus from the pulmonary artery. The pulmonary artery pressure for an unblocked artery may range from about 20 mmHg to about 35 mmHg though such a range may vary with age, fluid status and other underlying medical conditions. As such, the threshold value may be in the range from about 20 mmHg to about 35 mmHg.

In another embodiment, the method may include: (a) introducing a first guide wire into a venous access, (b) advancing the first guide wire through the vena cava, then through the right atrium, and ultimately into a pulmonary artery under fluoroscopic guidance, (c) advancing the apparatus over the first guide wire with the first guide wire passing through the first catheter until a distal end of the first catheter extends beyond the target lesion, (d) advancing a second guide wire through the second tubular housing until it arrives at the contralateral pulmonary artery, (e) advancing a second catheter over the second guide wire until the distal end of the second catheter extends beyond the target lesion, (f) advancing a treatment solution out of the at least one first outlet of the first catheter and the at least one second outlet of the second catheter and into the pulmonary arteries, and (g) monitoring the pulmonary artery pressure via the one or more pressure sensors.

In yet another embodiment, the method further includes the steps of determining, via the one or more pressure sensors, a blood pressure is greater than a threshold value, and in response to the determination that the blood pressure is greater than the threshold value, activating a pump to advance the treatment solution out of at least one of the first one or more outlets of the first catheter and the second one or more outlets of the second catheter. Such a method may further include the steps of determining, via the one or more pressure sensors, a blood pressure is less than a threshold value, and in response to the determination that the blood pressure is less than the threshold value, deactivating the pump. Such a method may be used to treat pulmonary hypertension or heart failure of a patient.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the following claims.

The invention claimed is:

1. An apparatus comprising:
a first catheter having a proximal end and a distal end, wherein a distal portion of the first catheter includes a first plurality of outlets;
a first lumen having a proximal end and a distal end, wherein the distal end of the first catheter extends distally past the distal end of the first lumen, wherein the first lumen comprises one or more pressure sensors at or near the proximal end of the first lumen and/or one or more pressure sensors at or near the distal end of the first lumen;
a second lumen having a proximal end and a distal end, wherein the distal end of the first catheter extends distally past the distal end of the second lumen; and
a second catheter having a proximal end and a distal end, wherein a distal portion of the second catheter includes a second plurality of outlets, wherein the distal end of the second catheter is configured to be positioned substantially within the second lumen when the second catheter is in a first position, and wherein the distal end of the second catheter is configured to extend through an opening in the distal end of the second lumen in a second position,
wherein the first catheter comprises a first number of lumens, and wherein the second catheter comprises a second number of lumens that is fewer than the first number of lumens,
wherein in the second position, the second catheter extends distal to the distal end of the first lumen, distal to the distal end of the second lumen, or distal to both the distal end of the first lumen and the distal end of the second lumen.

2. The apparatus of claim 1, wherein the second catheter includes a curved section that extends away from the distal end of the first lumen in an opposite direction from a curved section of the first catheter when the second catheter is in the second position.

3. The apparatus of claim 2, wherein the curved section of the first catheter has a radius of curvature in a range from about 3 cm to about 500 cm.

4. The apparatus of claim 1, wherein a length of the first catheter from the distal end of the first lumen to the distal end of the first catheter is in a range of about 3 cm to about 40 cm.

5. The apparatus of claim 1, further comprising:
a balloon coupled to the distal end of the first catheter.

6. The apparatus of claim 1, further comprising:
a pressure transducer line coupled to the one or more pressure sensors and positioned within the first lumen.

7. The apparatus of claim 1, wherein the distal portion of the first catheter has a length ranging from about 3 cm to about 40 cm, and wherein the distal portion of the second catheter has a length ranging from about 3 cm to about 40 cm.

8. The apparatus of claim 1, further comprising:
a first hemostatic valve disposed within each of the first plurality of outlets, and a second hemostatic valve disposed within each of the second plurality of outlets.

9. The apparatus of claim 1, further comprising:
a first pump coupled to at least one of the first catheter and the second catheter; and
a first reservoir coupled to the first pump.

10. The apparatus of claim 9, further comprising:
a volume sensor positioned in the first reservoir, wherein the volume sensor is configured to determine a volume of treatment solution remaining in the first reservoir; and
a wireless communication interface configured to transmit the determined volume to a computing device.

11. The apparatus of claim 9, wherein the first pump is coupled to the first catheter, and wherein the apparatus further comprises:
a second pump coupled to the second catheter, wherein the first reservoir is coupled to both the first pump and the second pump.

12. The apparatus of claim 9, wherein the first pump is coupled to the first catheter, and wherein the apparatus further comprises:
a second pump coupled to the second catheter, wherein the first reservoir is coupled to the first pump, and wherein a second reservoir is coupled to the second pump.

13. The apparatus of claim 12, wherein the first reservoir includes a first treatment solution and the second reservoir includes a second treatment solution.

14. The apparatus of claim 12, wherein the first reservoir has a first unique identifier and the second reservoir has a second unique identifier.

15. The apparatus of claim 1, wherein at least one pressure sensor of the one or more pressure sensors at least partially obstructs the first lumen.

16. The apparatus of claim 1, wherein at least one pressure sensor of the one or more pressure sensors extends distal to the distal end of the first lumen.

17. The apparatus of claim 1, wherein a cross-section of the first catheter, the first lumen, and the second lumen are positioned in a side-by-side linear configuration.

18. The apparatus of claim 1, wherein a cross-section of the first catheter, the first lumen, and the second lumen are positioned in a triangular configuration.

19. The apparatus of claim 1, wherein the distal end of the first catheter comprises a first curved section biased to have a curve in an unconstrained condition, and wherein the first curved section of the first catheter extends away from the distal end of the first lumen.

20. The apparatus of claim 1, wherein the second lumen is coupled to one or more of (i) the first catheter and (ii) the first lumen proximal to the first plurality of outlets of the first catheter.

21. A method comprising:
introducing the apparatus of claim 1 within a pulmonary artery;
introducing a guide wire into the second catheter of the apparatus;
moving the second catheter along the guide wire such that the distal end of the second catheter extends beyond the distal end of the first lumen; and
advancing a treatment solution out of both the first plurality of outlets of the first catheter and the second plurality of outlets of the second catheter and into the pulmonary artery.

22. The method of claim 21, further comprising:
after introducing the apparatus within the pulmonary artery, monitoring a blood pressure via the one or more pressure sensors; and
after advancing the treatment solution out of the first plurality of outlets of the first catheter and the second plurality of outlets of the second catheter, monitoring the blood pressure via the one or more pressure sensors.

23. The method of claim 21, further comprising:
inflating a balloon coupled to the distal end of the first catheter; and
advancing the distal end of the first catheter, via the balloon, from an inferior vena cava to a right ventricle, through a pulmonary valve to the pulmonary artery.

24. The method of claim 21, further comprising:
positioning the distal end of the first catheter into a first branch of the pulmonary artery;
advancing the distal end of the second catheter out of the distal end of the second lumen; and
positioning the distal end of the second catheter into a second branch of the pulmonary artery.

25. The method claim 21, further comprising:
determining a first blood pressure, via the one or more pressure sensors at a first time;
determining a second blood pressure, via the one or more pressure sensors at a second time later than the first time; and
comparing the first blood pressure to the second blood pressure to determine a change in blood pressure.

26. The method of claim 21, further comprising:
determining, via the one or more pressure sensors, a blood pressure is less than a threshold value corresponding to a normal blood pressure range; and
in response to the determination that the blood pressure is less than the threshold value, removing the apparatus from the pulmonary artery.

27. The method of claim 21, further comprising:
determining at a first time, via the one or more pressure sensors, a blood pressure is greater than a threshold value corresponding to a normal blood pressure range; and
in response to the determination that the blood pressure is greater than the threshold value, activating a pump to advance the treatment solution out of the first plurality of outlets of the first catheter and the second plurality of outlets of the second catheter.

28. The method of claim 27, further comprising:
determining at a second time later than the first time, via the one or more pressure sensors, a blood pressure is less than the threshold value; and
in response to the determination that the blood pressure is less than the threshold value, deactivating the pump.

* * * * *